(12) United States Patent
Jones et al.

(10) Patent No.: US 11,471,134 B2
(45) Date of Patent: Oct. 18, 2022

(54) INGESTIBLE DEVICE RECOVERY SYSTEM

(71) Applicant: Progenity, Inc., San Diego, CA (US)

(72) Inventors: Mitchell Lawrence Jones, La Jolla, CA (US); Christopher Loren Wahl, San Diego, CA (US); Alec John Lillis, Victoria (CA)

(73) Assignee: Biora Therapeutics, Inc., San Diego, CA (US)

( * ) Notice: Subject to any disclaimer, the term of this patent is extended or adjusted under 35 U.S.C. 154(b) by 741 days.

(21) Appl. No.: 16/464,739

(22) PCT Filed: Nov. 10, 2017

(86) PCT No.: PCT/US2017/061024
§ 371 (c)(1),
(2) Date: May 29, 2019

(87) PCT Pub. No.: WO2018/111466
PCT Pub. Date: Jun. 21, 2018

(65) Prior Publication Data
US 2019/0307434 A1 Oct. 10, 2019

Related U.S. Application Data

(60) Provisional application No. 62/434,188, filed on Dec. 14, 2016.

(51) Int. Cl.
*A61B 10/00* (2006.01)
*A61B 5/01* (2006.01)
(Continued)

(52) U.S. Cl.
CPC ............ *A61B 10/0096* (2013.01); *A61B 5/01* (2013.01); *A61B 5/036* (2013.01); *A61B 5/073* (2013.01);
(Continued)

(58) Field of Classification Search
CPC ............ A61B 10/0096; A61B 10/0038; A61B 10/0045; A61B 5/01; A61B 5/002; A61B 5/0031; A61B 5/0036; A61B 5/036; A61B 5/073; A61B 5/14539; A61B 5/15; A61B 10/02; A61B 1/041; A61B 5/0004;
(Continued)

(56) References Cited

U.S. PATENT DOCUMENTS 6,171,259 B1   1/2001  Fisher
8,696,602 B2   4/2014  Semler
(Continued)

FOREIGN PATENT DOCUMENTS

WO   WO-2006119371 A2 * 11/2006 ......... A61B 10/0045
WO   WO 2007034712       3/2007
WO   WO-2010057082 A2 *  5/2010 ............. A61B 1/041

OTHER PUBLICATIONS

International Search Report and Written Opinion in International Application No. PCT/US2017/061024, dated May 15, 2019.

*Primary Examiner* — Matthew Kremer
*Assistant Examiner* — Om Patel
(74) *Attorney, Agent, or Firm* — Procopio Cory Hargreaves and Savitch LLP

(57) ABSTRACT

Various embodiments are described herein for a recovery tool kit system including a recovery tool and an associated retrieval method for retrieving and storing an ingestible device.

16 Claims, 9 Drawing Sheets

(51) Int. Cl.
   *A61B 10/02* (2006.01)
   *A61B 5/145* (2006.01)
   *A61B 5/03* (2006.01)
   *A61B 5/07* (2006.01)
   *A61B 1/04* (2006.01)
   *A61B 10/04* (2006.01)
   *A61B 5/00* (2006.01)
   *A61B 5/06* (2006.01)

(52) U.S. Cl.
   CPC ...... *A61B 5/14539* (2013.01); *A61B 10/0038* (2013.01); *A61B 10/02* (2013.01); *A61B 1/041* (2013.01); *A61B 5/0004* (2013.01); *A61B 5/0031* (2013.01); *A61B 5/065* (2013.01); *A61B 5/6861* (2013.01); *A61B 10/04* (2013.01)

(58) Field of Classification Search
   CPC ....... A61B 5/065; A61B 5/6861; A61B 10/04; A61B 10/06; A61B 2017/00353; A61B 2017/00367; A61B 2017/00991; A61B 2017/22035; A61B 2017/22037; A61B 2017/2901; A61B 17/22031; A61B 17/221; A61B 17/28; A61B 17/50; A01N 1/02; B01L 3/50
   See application file for complete search history.

(56) References Cited

U.S. PATENT DOCUMENTS

| | | | |
|---|---|---|---|
| 2004/0175289 A1* | 9/2004 | Takizawa | A61B 1/041 4/256.1 |
| 2007/0066865 A1 | 3/2007 | Fukuda | |
| 2007/0260204 A1 | 11/2007 | Akagi | |
| 2012/0046682 A1* | 2/2012 | Nelson | A61B 17/1624 606/180 |
| 2012/0101481 A1 | 4/2012 | Wilson | |

\* cited by examiner

INGESTIBLE DEVICE RECOVERY SYSTEM

CROSS-REFERENCE TO RELATED APPLICATIONS

This application is a National Stage application under 35 U.S.C. § 371 of International Application No. PCT/US2017/061024, having an International Filing Date of Nov. 10, 2017, which claims the benefit of U.S. Provisional Ser. No. 62/434,188 filed Dec. 14, 2016. This disclosure of the prior applications are considered part of (and are incorporated by reference in) the disclosure of this application.

FIELD

Various embodiments are described herein for an apparatus, kit and method that may be used to retrieve an ingestible device after it has been evacuated from a body.

BACKGROUND

Ingestible devices can be used to take physiological measurements (e.g., measure pH) or provide imaging capabilities within the body of a person or animal. For example, such devices may be used to identify diseased areas of the gastrointestinal (GI) tract or collect samples thereof. While some ingestible devices may be capable of transmitting physiological and imaging data wirelessly, a user may be required to wear additional equipment to receive such a generally weak signal. As such it may be preferable to equip the ingestible device with sufficient on-board storage so that the data acquired by the ingestible device may be downloaded upon recovering the device after it is passed through the gastrointestinal tract and exits the body. However, recovering the device after it has been evacuated may pose challenges especially for those who are not trained or are not used to handling waste samples as the device must be recovered from the waste that is also evacuated form the body at the same time as the device is evacuated from the body.

SUMMARY OF VARIOUS EMBODIMENTS

Various embodiments of a recovery toolkit including a recovery tool and associated recovery methods are provided according to the teachings herein. The embodiments described herein are generally used to recover an ingestible device after it has been evacuated from a user's body.

In a broad aspect, at least one embodiment described herein provides a recovery tool for retrieving and storing an ingestible device, wherein the recovery tool comprises a collection member with an open end, a closed end and a collection chamber therebetween for receiving the ingestible device after recovery; and a cap assembly releasably attachable to the open end of the collection member to seal the collection chamber, the cap assembly comprising a closure portion; a handle extending from the closure portion in a first direction; a shaft extending from the closure portion in a second direction that is opposite the first direction; an extension shaft moveably coupled to the shaft and having a distal end portion, the extension shaft being moveable between a retracted position in which the extension shaft is disposed within the shaft and an extended position in which the distal end portion of the extension shaft is extended away from the shaft in a telescopic manner; and a retriever being disposed at the distal end portion of the extension shaft and adapted to retrieve the ingestible device.

In at least one embodiment, the extension shaft is slidably coupled to the shaft allowing the extension shaft to be moveable in a telescopic fashion.

In at least one embodiment, the extension shaft comprises at least two sections that are pivotally coupled to one another to allow the extension shaft to be moveable in a pivotable fashion.

In at least one embodiment, the retriever comprises a magnet disposed in the distal end portion of the extension shaft and adapted to retrieve the ingestible device by applying a magnetic attraction force.

In at least one embodiment, the closed end of the collection member is shaped to align the ingestible device with the magnet to turn the ingestible device off.

In at least one embodiment, the closed end of the collection member comprises additional packaging to protect and/or to preserve samples within the ingestible device.

In at least one embodiment, the retriever comprises one of mechanical forceps, graspers, a pliable loop, adhesive means, a suction tip and a vacuum.

In at least one embodiment, the recovery tool further comprises a locking mechanism that maintains the extension shaft in the retracted position and is actuable to allow movement of the extension shaft to the extended position.

In at least one embodiment, the locking mechanism comprises a first aperture on a surface of the shaft, a second aperture on a surface of the extension shaft and a boss disposed within the shaft extension and positioned at the second aperture to engage and disengage the first aperture during use.

In at least one embodiment, the boss comprises a body having a leaf spring to maintain the boss in position within the extension shaft.

In at least one embodiment, when the extension shaft is in the extended position, the extension shaft is moveable to the retracted position by pushing the distal end of the cap assembly against an inner portion of the collection chamber.

In at least one embodiment, the recovery tool further comprises a controller to control one or more electronic aspects of the recovery tool; and at least one sensor coupled to the controller and operable to detect a parameter of the environment of the collection chamber after storage of the retrieved ingestible device.

In at least one embodiment, the at least one sensor comprises at least one of a pressure sensor, a temperature sensor and a humidity sensor.

In at least one embodiment, the controller is configured to monitor and record an elapsed time duration in which the retrieved ingestible device has been stored in the collection chamber.

In at least one embodiment, the recovery tool further comprises a transceiver coupled to the controller, the transceiver being configured for receiving a beacon signal from the ingestible device when the ingestible device is in close proximity to the recovery tool and also configured to transmit a second signal to the ingestible device to acknowledge the ingestible device has been detected.

In at least one embodiment, the controller is configured to operate the recovery tool is low power mode upon retrieval of the ingestible device.

In at least one embodiment, the controller is configured to operate the at least one sensor for monitoring a condition of the ingestible device upon retrieval of the ingestible device.

In at least one embodiment, the collection member and the cap assembly form a seal when releasably secured to one another to prevent any fluid from escaping from or entering into the collection chamber.

In another broad aspect, at least one embodiment described herein provides a recovery kit for retrieving an ingestible device after the ingestible device is evacuated from a user's body, wherein the recovery kit comprises a recovery tool as defined according to any of the teachings herein; and a carrying case dimensioned to receive the recovery tool.

In at least one embodiment, the recovery kit further comprises a shipping package for receiving the recovery tool after the ingestible device has been recovered and stored in the recovery tool and being useable for shipping the recovery tool with the recovered ingestible device to a processing/analysis facility.

In at least one embodiment, the shipping package and the recovery tool are made from materials that are compliant with UN3373 regulations related to medical packaging and shipment of category B materials.

In at least one embodiment, the recovery kit further comprises instructions for use of the recovery tool; a pair of gloves for handling the recovery tool during use; and a plastic bag for receiving the recovery tool after the ingestible device has been recovered and prior to placing the recovery tool with the stored ingestible device into the shipping package, where the plastic bag is watertight.

In at least one embodiment, the recovery kit further comprises a collection tray for collecting fecal matter that includes the ingestible device after the ingestible device has been evacuated from the user's body.

In at least one embodiment, the collection tray comprises a first pair of adhesive strips for attaching a pair of first portions of the collection tray to opposite arms of a toilet seat and a second pair of adhesive strips for attaching a pair of second portions of the collection tray to opposite sides of a toilet bowl.

In another broad aspect, at least one embodiment described herein provides a method of recovering an ingestible device after the ingestible device exits a user's body, wherein the method comprises separating a collection member from a cap assembly of a recovery tool; extending an extension shaft of the cap assembly from a retracted position to an extended position; retrieving the evacuated ingestible device using a distal end of the extension shaft; inserting the extension shaft with the ingestible device into a collection chamber of the collection member; moving the extension shaft from the extended position to the retracted position; and releasably mounting the cap assembly to the collection member, the collection member and the cap assembly providing a water tight environment for the ingestible device and the extension shaft disposed in the collection chamber.

In at least one embodiment, the method comprises mounting a collection tray to a toilet in order to receive excreted fecal matter including the evacuated ingestible device from the user, the act or mounting comprising attaching a first pair of adhesive strips on a first pair of bottom portions of the collection tray to opposite arms of a toilet seat; and attaching a second pair of adhesive strips on a second pair of bottom portions of the collection tray to opposite sides of a toilet bowl.

In at least one embodiment, the method further comprises placing the recovery tool with the stored ingestible device into a shipping package; and sending the shipping package to a processing/analysis facility.

In at least one embodiment, the method further comprises placing the recovery tool with the stored ingestible device into a plastic bag; placing the plastic bag with the recover tool and stored ingestible device into a shipping package; and sending the shipping package to a processing/analysis facility.

In at least one embodiment, the method comprises using a magnet at the distal end of the extension shaft to retrieve the evacuated ingestible device.

In at least one embodiment, the method comprises using one of mechanical forceps, graspers, a pliable loop, adhesive means, a suction tip and a vacuum at the distal end of the extension shaft to retrieve the evacuated ingestible device.

In at least one embodiment, the method further comprises receiving a beacon signal from the evacuated ingestible device using a transceiver that is electrically coupled with the recovery tool, the beacon signal indicating that the evacuated ingestible device is in close proximity to the recovery tool.

In at least one embodiment, the method further comprises using the transceiver to transmit a second signal to the evacuated ingestible device upon receiving the beacon signal to acknowledge that the ingestible device has been detected.

In at least one embodiment, the method further comprises operating the recovery tool in low power mode upon retrieval of the ingestible device.

In at least one embodiment, the method further comprises operating at least one sensor for monitoring a condition of the ingestible device upon retrieval of the ingestible device.

In at least one embodiment, the method further comprises using a humidity sensor for monitoring humidity of the collection chamber during storage and/or transportation of the recovered ingestible device.

In at least one embodiment, the method further comprises using a temperature sensor for monitoring temperature of the collection chamber during storage and/or transportation of the recovered ingestible device.

In at least one embodiment, the method further comprises using a counter or a controller for monitoring elapsed time for storage and/or transportation of the recovered ingestible device.

In at least one embodiment, the method comprises using a recovery tool as further defined in any one of teachings herein.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

At least another embodiment described herein includes a recovery tool for retrieving and storing an ingestible device. The recovery tool includes a collection member having an open end, a closed end and a collection chamber between the open end and the closed end for receiving the ingestible device after recovery. The recovery tool further includes a cap assembly releasably attachable to the open end of the collection member to seal the collection chamber. In some embodiments, the cap assembly includes a sensor configured to receive a beacon signal from an ingestible device and detect a proximity of the ingestible device based on the beacon signal, a transceiver configured to transmit a signal to the ingestible device, and a shaft extending from the closure portion to retrieve the ingestible device.

At least another embodiment described herein includes a method of recovering an ingestible device after the ingestible device exits a user's body. A beacon signal is received, via a sensor at a recovery tool, from an ingestible device. The ingestible device is determined to be in proximity for recovery based at least in part on the beacon signal. A triggering signal is transmitted, via a transceiver at the recovery tool, to the ingestible device to initiate an action by the ingestible device. The ingestible device is then recovered, via the recovery tool.

In at least one embodiment, a first signal is transmitted to the ingestible device, and the first signal includes any of a light signal, an audio signal or a wireless electromagnetic signal.

In at least one embodiment, the beacon signal is received at a user device to notify the user that the ingestible device has been evacuated from a human body.

In at least one embodiment, the action by the ingestible device includes generating a visual signal or an audio signal by the ingestible device.

In at least one embodiment, the action by the ingestible device includes any of data transfer from the ingestible device to the recovery tool, or configuring a low power mode with the ingestible device.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

Figure 1A:
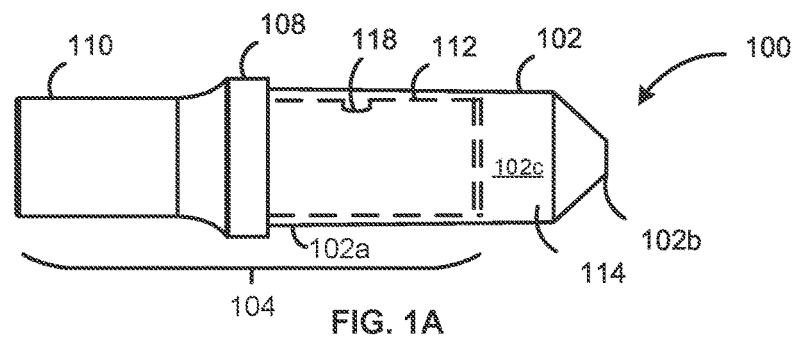
FIGS. 1A-1D are diagrams showing various side views of an example embodiment of a recovery tool for recovering an ingestible device in accordance with the embodiments described herein.

Further aspects and features of the example embodiments described herein will appear from the following description taken together with the accompanying drawings.

DETAILED DESCRIPTION OF THE EMBODIMENTS

Various embodiments in accordance with the teachings herein will be described below to provide an example of at least one embodiment of the claimed subject matter. No embodiment described herein limits any claimed subject matter. The claimed subject matter is not limited to devices or methods having all of the features of any one of the devices or methods described below or to features common to multiple or all of the devices and or methods described herein. It is possible that there may be a device or method described herein that is not an embodiment of any claimed subject matter. Any subject matter that is described herein that is not claimed in this document may be the subject matter of another protective instrument, for example, a continuing patent application, and the applicants, inventors or owners do not intend to abandon, disclaim or dedicate to the public any such subject matter by its disclosure in this document.

It will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have a mechanical, magnetic or electrical connotation. For example, as used herein, the terms coupled or coupling can indicate that two elements or devices can be directly connected to one another or connected to one another through one or more intermediate elements or devices via a magnetic signal, an electrical signal or a mechanical element, depending on the particular context.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term if this deviation would not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed, such as 10%, for example.

Ingestible devices may be swallowed by a person or animal (hereafter referred to as a user) and be used to perform analysis or physiological measurements, collect biological samples or deliver therapeutic agents as it passes through the digestive or GI tract of the user's body. Accordingly, the term ingestible device, as used herein, is meant to cover an electronic-based or mechanical-based ingestible device which may be in the form of a capsule or a similar size as some larger pharmaceutical capsules. In circumstances in which an ingestible device is used for any of the above purposes, or for environmental considerations, there may be a desire to retrieve the ingestible device after the ingestible device has been evacuated, excreted or exited (hereafter referred to as evacuated) from the user's body.

The process of retrieving the ingestible device from excreted waste may pose a challenge for sanitary and other reasons. Additionally, if the ingestible device was recovered outside of a laboratory/facility equipped to retrieve and process the ingestible device, the retrieved device may also have to be transported to a processing/analysis facility or laboratory in a manner that complies with local laws and regulations with respect to the transportation of biological samples. In accordance with the teachings herein, various embodiments are provided of a device, a method and a kit that may be used for the efficient and safe recovery and transportation of an ingestible device.

Figure 1B:
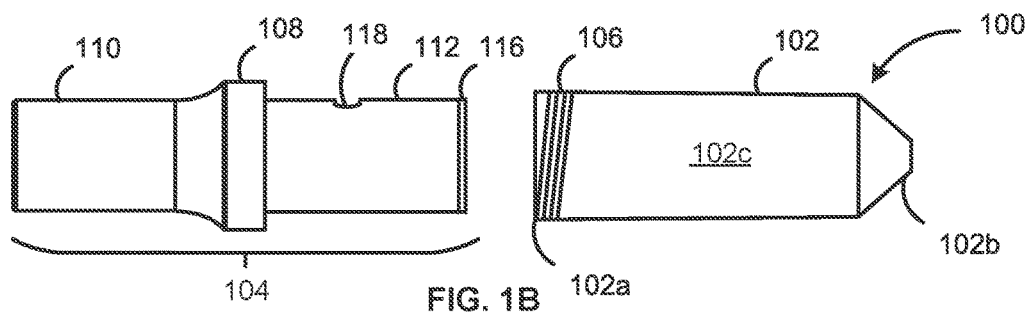
Figure 1C:
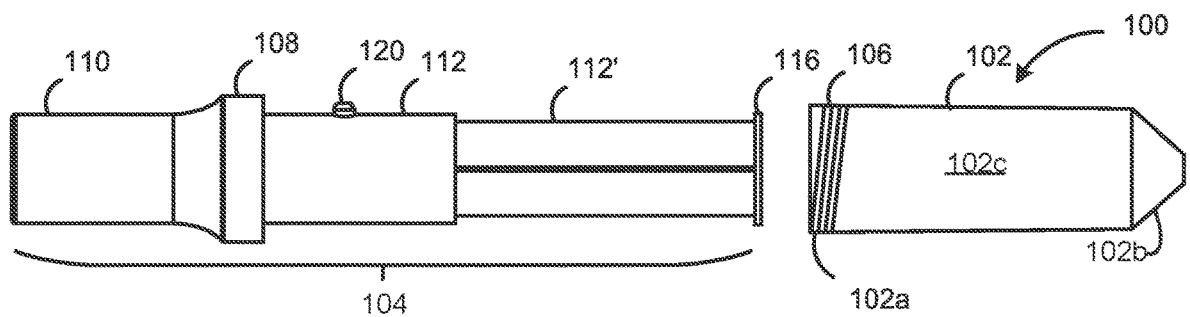
Figure 1D:
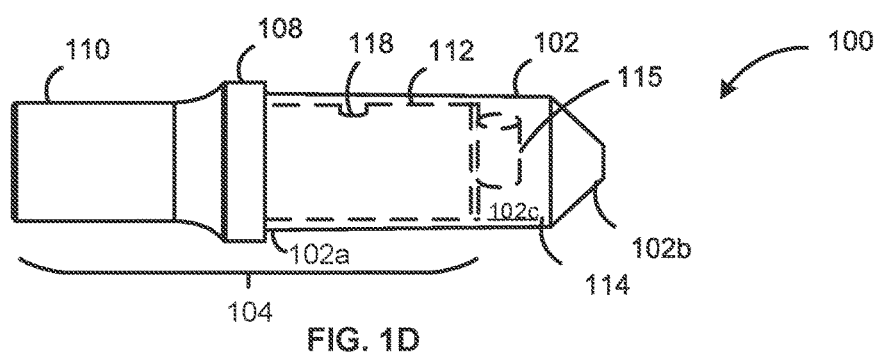

Referring now to FIGS. 1A to 1D, illustrated therein is a diagram are various side views of an example embodiment of a recovery tool 100 for recovering an ingestible device in accordance with the teachings herein. In particular, FIG. 1A shows the recovery tool 100 in a closed configuration before use, FIGS. 1B and 1C show the recovery tool in an open configuration before use and FIG. 1D shows the recovery tool in a closed position after use (i.e. after the ingestible device has been recovered).

The recovery tool 100 comprises a collection member 102 and a cap assembly 104. The collection member 102 has an open end portion 102a, a closed end portion 102b and a collection chamber 102c for receiving and storing the recovered ingestible device (shown in hashed lines as device 115 in FIG. 1D). The cap assembly 104 can be releasably attached or secured to the collection member 102 to close the open end portion 102a of the collection member 102. The collection member 102 and the cap assembly 104 are made using water-resistant materials such that they make a watertight seal when secured to one another.

In some embodiments, the collection member 102 may be a tube made of a biologically compatible material such as polyethylene or polystyrene material. For example, the collection member 102 may be a conical centrifuge tube such as a Falcon™ 50 mL conical centrifuge tube. The closed end portion 102b of the collection member 102 may have a conical end to provide room for the recovered ingestible device when a distal portion of the cap assembly 104 includes the recovered ingestible device and is being inserted into the collection member 102. In some embodiments, the closed end portion 102b of the collection member 102 may be cylindrical. In other embodiments, the closed end portion 102b of the collection member 102 may be round or spherical. In other embodiments, the closed end portion 102b may have one or more of solid portions to provide additional packaging to protect and/or to preserve samples within the ingestible device. Alternatively, or in addition thereto the closed end portion 102b may have structural features and/or be shaped to position or align the recovered ingestible device with a magnet at the extension shaft which acts as a magnetic off switch to turn the ingestible device off after it has been recovered.

The open end 102a of the collection member 102 may be releasably sealed by the cap assembly 104 using different mechanisms. In this example embodiment, the exterior surface of the open end portion 102a has threads 106a and a closure portion 108 of the cap assembly 104 has corresponding grooves or internal threading 106b (shown as element 122 in FIG. 2) so that the cap assembly 104 can be screwed (i.e. releasably secured) onto the open end portion 102a of the collection member 102 to seal the collection chamber 102c. This particular closure mechanism of using threads and grooves allows the collection member 102 to be sealed more securely by the cap assembly 104. In some embodiments, the closure portion 108 may be regarded as a modified screw-on cap that is normally associated with a collection tube (e.g. the Falcon™ 50 mL conical centrifuge tube).

Alternatively, in other embodiments, other closure elements can be used. For example, the exterior of the open end portion 102a of the collection member 102 and the closure portion 108 of the cap assembly 104 may be dimensioned to provide a friction fit. For example, the exterior portion of the open end portion 102a can have a flange that acts as a stop mechanism when the closure portion 108 of the cap assembly 104 is releasably mounted to the collection member 102. The inner surface of the closure portion 104 can have a smooth surface. Alternatively, the inner surface of the closure portion 104 can have a fingers or tabs for releasably engaging the flange of the open end portion 102a. Alternatively, other press-fitting mechanisms such as, but not limited to, ball detents or any means for securely fastening a cap to a tube or container, for example, may be used for at least one of the open end portion 102a of the collection member 102 and the closure portion 108 of the cap assembly 104.

The cap assembly 104 further comprises a handle 110 and a shaft 112. The handle 110 extends away from the collection member 102 and provides a gripping surface for a user to handle the recovery tool 100 and attach or detach the cap assembly 104 from the collection member 102, as will be described in more detail below. The shaft 112 extends from the closure portion 108 towards the collection member 102. The shaft 112 is used to recover the ingestible device from excreted waste, as will be described in more detail below.

The shaft 112 may be cylindrical or it may have a different cross-sectional shape in other embodiments such as, but not limited to, rectangular, square, triangular or cross-shaped, for example. The outer circumference of the shaft 112 is smaller than the inner circumference of the collection chamber 102c so that the shaft 112 fits inside the collection chamber 102c when the cap assembly 104 is releasably secured to the collection member 102. Likewise, the length of the shaft 112 is chosen so that it is shorter than the length of the collection chamber 102c. In doing so, the shaft 112 can be inserted into the collection chamber 102c when the cap assembly 104 is releasably secured to the collection member 102, as shown in FIG. 1A. However, it can be noted that the shaft 112, as denoted by hashed lines, does not occupy the entire volume of the collection chamber 102c. Additional space 114 may be reserved so as to provide room for the recovered ingestible device 115 as well as a portion of excreted waste that may be attached to the recovered ingestible device 115.

Referring now to FIG. 1C, the shaft 112 comprises an extendable extension shaft 112' with a lip 116 at its distal end. The extension shaft 112' can be in a retracted position (see FIGS. 1B and 1D) in which the extension shaft 112' resides coaxially within the shaft 112. The extension shaft 112' can also be in an extended position (see FIG. 1C) in which the lip 116 is extended away from the shaft 112. The lip 116 may be gripped by a user of the recovery tool 100 to manually pull the extension shaft 112' to move the extension shaft from the retracted position to the extended position. The extendable shaft 112' thus provides a telescoping "wand" or telescoping "arm" to help improve access to the ingestible device when the ingestible device must be recovered from evacuated fecal matter. In this way, the recovery tool 100 with the extended shaft 112' reduces risk of the user coming in contact with the evacuated fecal matter. Accordingly, the extension shaft 112' is slidably coupled to the shaft 112 allowing the extension shaft 112' to be moveable in a telescopic fashion.

In an alternative embodiment, the extension shaft 112' may comprise at least two sections that are pivotally coupled to one another to allow the extension shaft to be moveable in a pivotable fashion. In an alternative embodiment, the extension shaft 112' may include several extensible sections that are connected telescopically or pivotally such that the extension shaft 112' may be further extended.

The length of the extension shaft 112' can be chosen such that that when the extension shaft 112' is retracted, the lip 116 sits flush with the open edge of an outer wall of the shaft 112 as shown in FIG. 1B. Alternatively, in other embodiments, the extension shaft 112' may have a length such that the lip 116 is disposed away from the outer wall of the shaft 112 when the extension shaft 112' is in the retracted position but the lip 116 can still fit within the collection chamber 102c when the cap assembly 104 is secured to the collection member 102. However, the cap assembly 104 can be used with the extension shaft in either the retracted position or the extended position depending on the user's preference. Alternatively, in other embodiments, the shaft 112 may not have the extension shaft 112' and the length of the shaft 112 is to maintain separation between the excreted fecal matter and the retrieval person during the retrieval process.

The shaft 112 and the extension shaft 112' may be dimensioned such that there is a friction fit between these two elements that allows the user to move the extension shaft 112' relative to the shaft 112 from a first position to a second position and stay in the second position while the user uses the recovery tool 100 to recover the evacuated ingestible device.

Alternatively, as shown in FIGS. 1A-1D, the shaft 112 may comprise an opening or aperture 118 through which a boss (i.e. a button, tab, or post) 120 located on the outer wall of the extension shaft 112' may extend, when the extension shaft 112' is fully moved to the extended position, as the user pulls on the lip 116 with one hand and holds onto the handle 110 with their other hand. When the extension shaft 112' is fully extended the boss protrudes through the opening 118 and provides a locking mechanism to maintain the extension shaft 112' in the extended position. Conversely, the boss 120 on the outer wall of the extension shaft 112' provides resistance against the inner wall of the shaft 112, when the extension shaft 112' is in the retracted position. In this way, the extension shaft 112' is secured within the shaft 112, and does not unintentionally slip away from the shaft 112. To retract the extension shaft 112', the user depresses the boss 120 and exerts a force on an end of the extension shaft 112' (i.e. at a portion of the lip 116) to slide the extension shaft 112' back into the shaft 112.

In an alternative embodiment, the boss 120 may extend through the aperture 118 to secure a retracted position, e.g., when the extension shaft 112' is at least partially within the shaft 112. The user may depress the boss 120 and pull the extension shaft 112' away from the shaft 112 into the extended position. At the extended position, the boss 120 is disposed within the extension shaft 112' and provides an outward force to hold the extension shaft 112' in place. The user can then retrieve the evacuated ingestible device. Once the ingestible device is obtained, a force may be exerted on a portion of the lip 116 to move the extension shaft 112' back into the retracted position at which point the boss 120 may protrude through the aperture 118 to hold the extension shaft 112' in the retracted position.

The distal end portion of the extension shaft 112' (i.e. near the lip 116) may be equipped with a collection mechanism. For example, for retrieving an ingestible device with a built-in magnet or ferromagnetic materials, the distal end portion of the extension shaft 112' may comprise a recovery magnet (shown as element 124 in FIG. 2) that is used to collect the ingestible device using magnetic attraction. In some embodiments, a disk magnet can be embedded into the distal end of the extension shaft 112' to provide the necessary magnetic force. Alternatively, the recovery magnet can be mounted onto the end of the extension shaft 112' using a suitable bonding agent.

The recovery magnet is selected to provide a certain amount of pull force that is sufficient given the dimensions and weight of the ingestible device that is to be retrieved. For example, a D83 disk magnet with a diameter of 0.5 inches may be used to impart about 9 lbs of pull force. Alternatively, a D96 disk magnet with a diameter of 0.5 inches may be used to impart about 16.5 lbs of pull force. In another alternative, a Dx82 disk magnet with a diameter of 1.5 inches may be used to impart about 20.4 lbs of pull force. In yet another alternative, a Dx84 disk magnet with a diameter of 1.5 inches may be used to impart about 34 lbs of pull force.

The entire recovery tool 100 can be made to be relatively compact, since the cap assembly 104 and the collection chamber 102c can be combined into a single unit as shown in FIG. 1A prior to use as well as during transportation after the ingestible device has been recovered and stored within the recovery tool 100 as is shown in FIG. 1D. The collection chamber 102c can have various dimensions to accommodate different sized ingestible devices. For example, the collection chamber 102c may have a length of about 5 mm to about 120 mm, a diameter of about 12 mm to about 30 mm and a volume of about 15 ml to about 50 ml but it may be sized differently in different embodiments. Furthermore, the recovery tool 100 can be made of materials that can be sterilized such as, but not limited to, polypropylene, for example.

Figure 2:
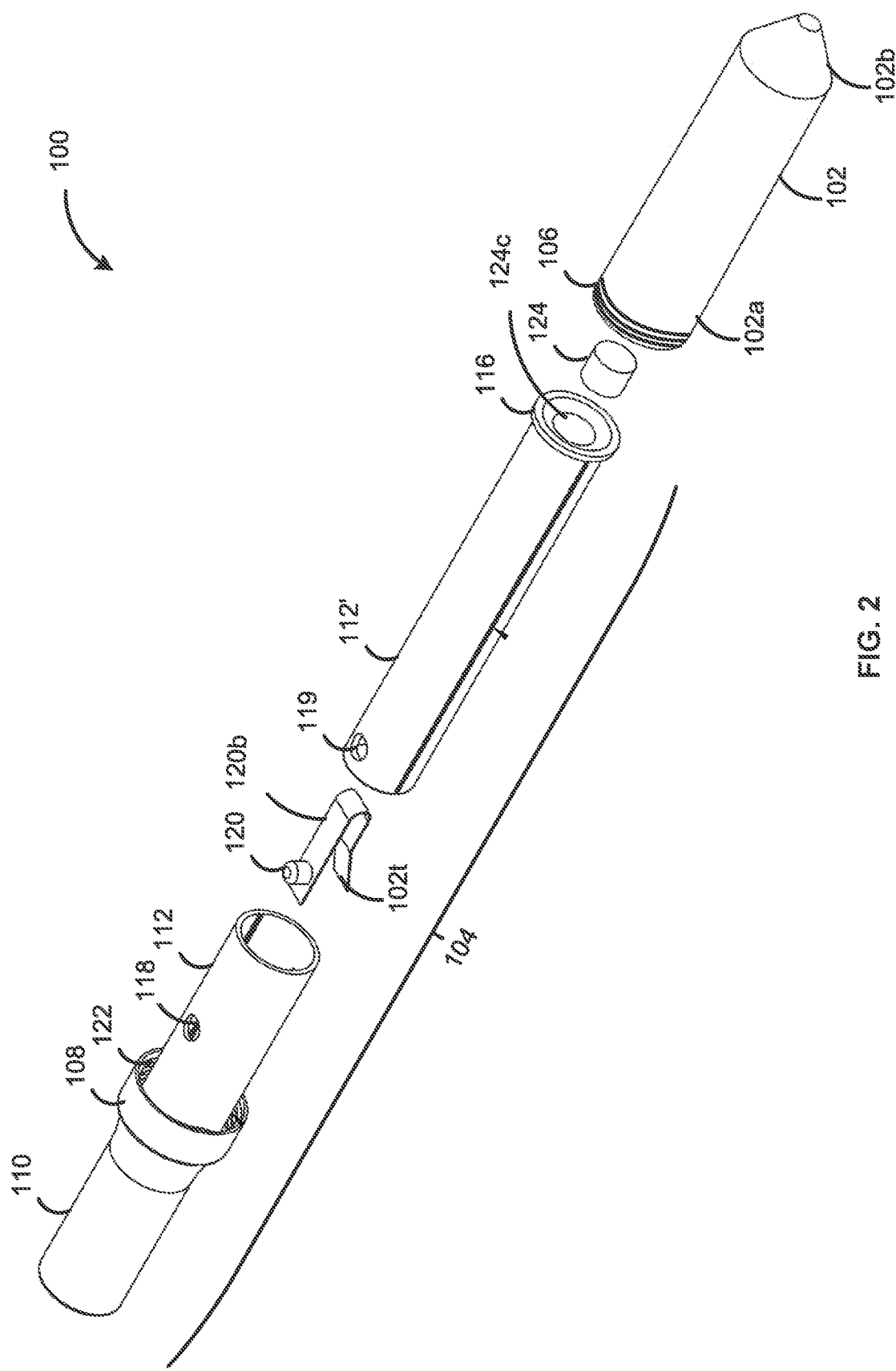
FIG. 2 is a diagram of an exploded view of an embodiment of the recovery tool in accordance with the embodiments described herein.

Referring now to FIG. 2, shown therein is an exploded view of the recovery tool 100 and its various components. Visible in FIG. 2 is the boss 120, and internal threading 122 of the closure portion 108 that allows the cap assembly 104 to releasably engage (i.e. screw onto) the threaded surface 106 of the collection member 102. The locking mechanism to maintain the extension shaft 112' in the retracted position within the shaft 112 comprises the first aperture 118 on a surface of the shaft 112, a second aperture 119 on a surface of the extension shaft and the boss 120. The boss 120 has a body 120b that provides a friction fit within the shaft 112 to keep the boss 120 in place. In this embodiment, the body 120b of the boss 120 is a leaf spring that has a tip 120t that can be mounted to an internal portion of the shaft 112 (e.g. there may be a groove on an internal surface of the shaft 112 that can be engaged by the tip 120t of the boss 120. Furthermore, recovery magnet 124 is installed at the distal end of the extension shaft 112' (or the shaft portion 112 in embodiments in which there is no extension shaft 112'). The recovery magnet 124 may be disposed within a channel 124c and in place using a friction fit at the distal end of the extension shaft 112' near the lip 116.

Figure 3:
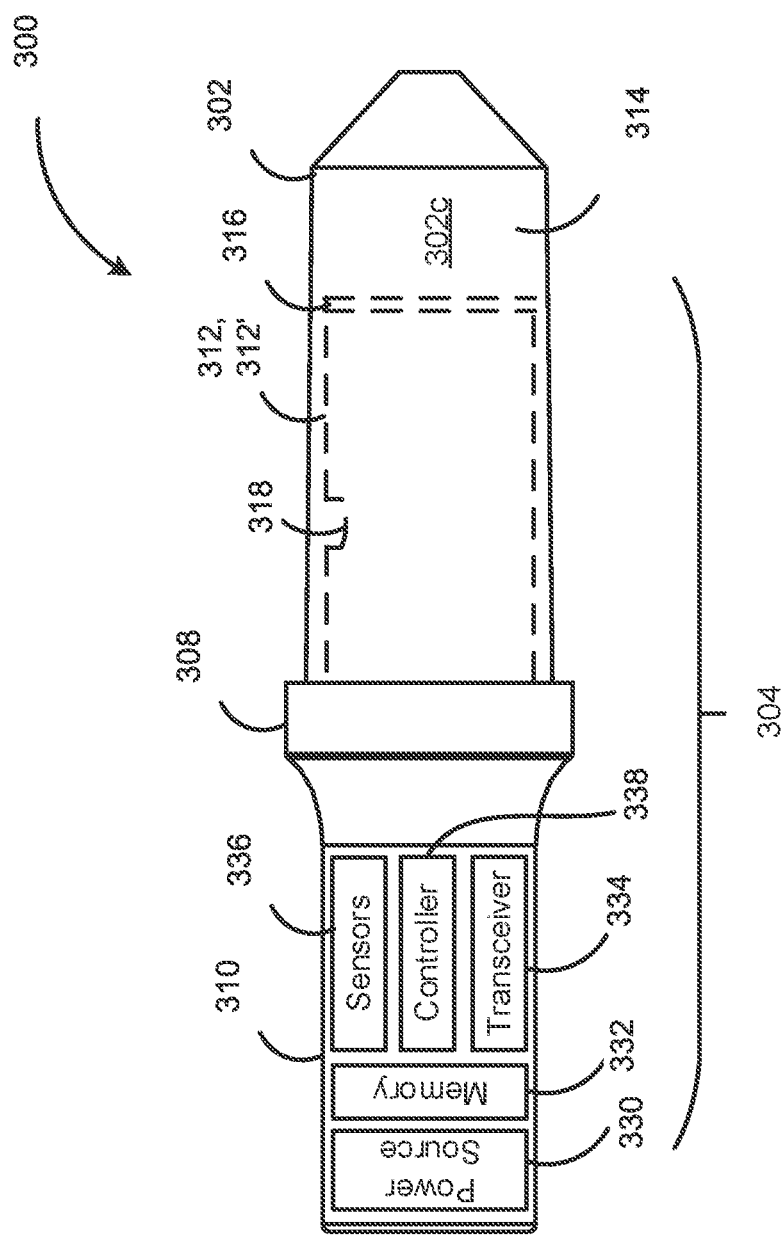
FIG. 3 is a diagram of an alternative embodiment of a recovery tool for recovering an ingestible device in accordance with the embodiments described herein.

Referring now to FIG. 3, shown therein is an alternative example embodiment of an ingestible device recovery tool 300. The elements that are common to both recovery tools 100 and 300 are shown using similar reference numbers. The recovery tool 300 can be regarded as being substantially similar to the recovery tool 100 in terms of physical structural elements and features. However, the handle 310 of the recovery tool 300 comprises electronic components to assist in the identification of the excreted ingestible device as well as the monitoring of certain conditions. In other embodiments, the electronic components may be embedded within other areas of the recovery tool 300. In yet other embodiments, the electronic components may be a separate device that can be attached to the recovery tool 300. In this regard, in an alternative embodiment a separate attachable device that provides the functionality of these electronic components may be used in conjunction with the recovery tool 100.

The electronic components may be soldered onto a printed circuit board (not shown) that is small enough to fit into the handle 310. In some embodiments the circuit board may be a flexible circuit board to permit easier disposition of the electronic components within the handle 310. The electronic components generally comprise a power source 320, memory 332, a transceiver 334, one or more sensors 336 and a controller 338.

The power source 330 may be a battery such as a button battery that can fit within a confined space. In some cases the power source 330 may be rechargeable. The power source 330 is selected to provide sufficient power for the operation of the other electronic components.

One or more sensors 336 may be included to monitor the conditions inside and outside the collection chamber 302c, for example, when the recovered ingestible device is stored inside the collection member 302 and during transportation to a processing facility. For example, the sensors 336 may comprise at least one of a temperature sensor, a pressure sensor and a humidity sensor for determining the environmental conditions of the stored recovered ingestible device in order to determine if the environmental parameters are suitable for the recovered ingestible device (i.e. to monitor the temperature and/or humidity to see if they are within acceptable ranges or are too high or too low). In some embodiments, the controller 338 may have an onboard temperature to monitor ambient temperature during storage of the recovered ingestible device as well as shipping of the recovered ingestible device. The monitored conditions may be recorded and saved to the memory 332 and retrieved at a processing facility for quality control or record keeping. The memory 332 can be implemented using any suitable memory technology that provides sufficient storage capacity and speed of access for environmental data or other data that is recorded and/or accessed by the controller 338.

The controller 338 can be implemented using a processor, an Application Specific Integrated Circuit (ASIC), Field Programmable Gate Array (FPGA) or Digital Signal Processor (DSP) that can provide sufficient processing power for the operation of the recovery tool 100. The controller 338 may be programmed to coordinate the monitoring and recording of the environmental conditions, and also to track the time at which the recordings are made. The recorded environmental conditions can later be evaluated to determine if the samples have been stored and shipped correctly under proper conditions. In addition thereto, or alternatively, in some embodiments, the controller 338 may activate the transceiver 334 to transmit a signal upon determining that the environmental conditions are not suitable for the stored recovered ingestible device and that corrective action is required. Additionally, the controller 338 may also track the elapsed time since the evacuated ingestible device has been stored in the recovery tool 300 and/or the elapsed time that the recovery tool with the evacuated ingestible device has spent while being shipped to the processing/analysis facility. In some embodiments, a counter may be used to determine the elapsed time. In some embodiments, the controller 338 may also be configured to track the charge level of the power source 330. If the time spent in storage or shipping is too long and/or the battery power is at critical low levels, the controller 338 may active the transceiver 334 for transmitting this data to the processing facility so that corrective action may be taken. While the various electronic components are depicted separately in FIG. 3, it may be noted that two or all of the components can be combined into a single integrated circuit such as a System-on-a-Chip (SoC) device to further save on space use.

The sensors 336 may further include an exit sensor to assist with identifying and locating the ingestible device after it has evacuated the user's body and is being recovered using the recovery tool 300. When the exit sensor has located the evacuated ingestible device, the controller 338 can instruct the transceiver 334 to send a first signal to the ingestible device. In some embodiments, the ingestible device may be programmed to generate and transmit a second signal, such as a beacon signal, when it has received the first signal from the recovery tool 300. The first signal may be a light signal (e.g. infrared, near infrared or visible light), an audio signal or a wireless electromagnetic signal such as an RF signal that can be detected by the ingestible device. The type of signal that is transmitted by the recovery tool 300 depends on the type of sensors used by the ingestible device. For example, the ingestible device may have various LED sensors and the recovery tool may generate a light signal (in this case the ingestible device comprises a light generator, not shown) having a particular color that is detectable by the ingestible device.

Figure 8:
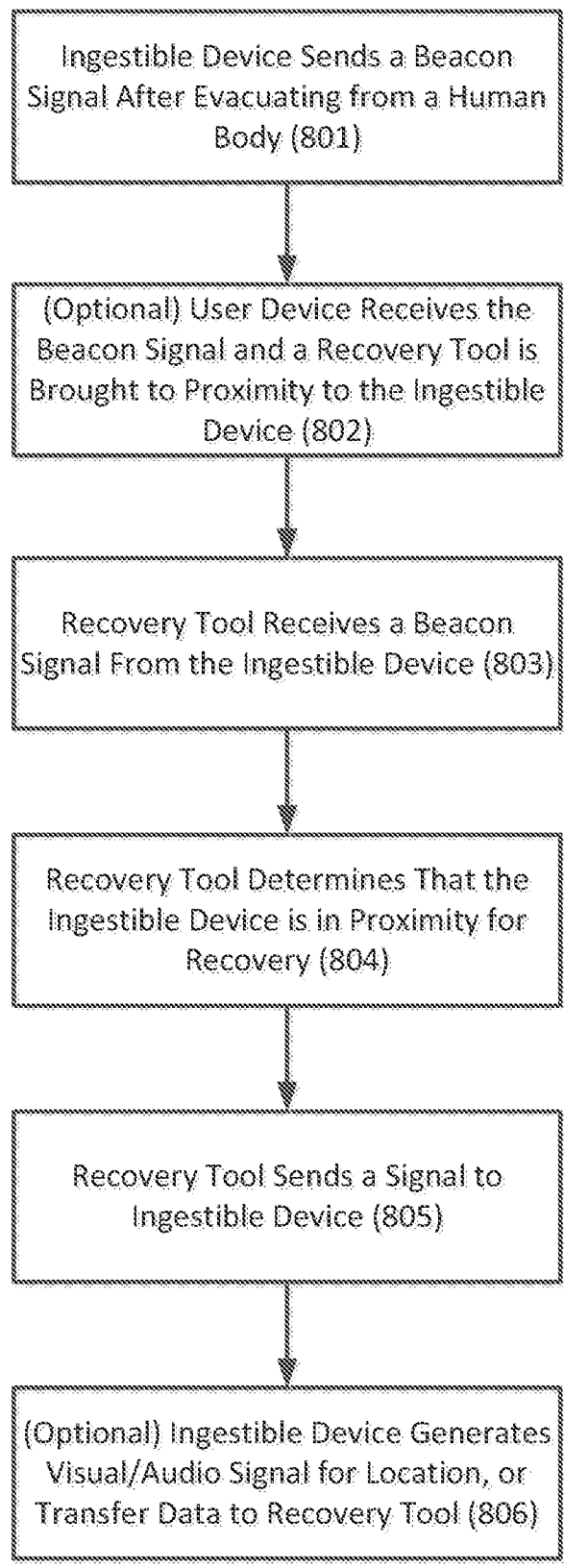
FIG. 8 is a flowchart of an example embodiment of a recovery method that can be used by operating the recovery tool 300 as shown in FIG. 3.

In an alternative embodiment, as illustrated in FIG. 8, at 801 the beacon signal may be generated (i.e. triggered) and transmitted from the ingestible device to the recovery tool after the ingestible device has been evacuated from the human body, e.g., without the recovery tool sending the first signal to the ingestible device. Alternatively, the ingestible device may optionally send the beacon signal to another device (a "user device") such as, but not limited to, a computer, a laptop, a tablet, a smart phone, and a wearable device to notify a retrieval person that the ingestible device has been evacuated. For example, the user device may receive the beacon signal such that a retrieval person may bring the recover tool to a proximity of the ingestible device, at 802. The ingestible device may generate and transmit the beacon signal when it determines that it has bene evacuated which may be determined when the temperature detected by the ingestible device suddenly drops. In other cases the beacon signal may be generated and transmitted when the temperature surrounding the ingestible device no longer corresponds to temperatures that are expected within the user's body. In another embodiment, the beacon signal may be generated and transmitted by the ingestible device when an increase in ambient light is detected. Alternatively, in another embodiment, the beacon signal may be generated and transmitted by the ingestible device when a decrease in temperature and an increase in ambient light have been detected. In another embodiment, the beacon signal may be generated and transmitted when the ingestible device detects a series of pressure changes consistent with the ingestible device exiting the body, for example, as described in U.S. Pat. No. 8,696,602. The device that receives and detects the beacon signal may be configured to notify the user that a beacon signal has been detected. At 803, upon receiving the beacon signal from the ingestible device, the recovery tool may determine that the ingestible device has been detected, e.g., at 804.

In some embodiments, upon evacuation, the ingestible device may generate a visual signal (i.e. flashing lights) or an audio signal (beeping sound) that is to allow the person retrieving the ingestible device to visually or to acoustically identify the location of the evacuated ingestible device to make retrieval easier. Or alternatively, the recovery tool may send a first signal to the ingestible device at 805. In response to the first signal, the ingestible device may be triggered to generate such visual or audio signals when a first signal is received from the recovery tool, e.g., the recovery tool is within proximity to recover the ingestible device, at 806.

In some embodiments, the sensors 336 include a proximity sensor (or the exit sensor may also operate as a proximity sensors) and the beacon signal that is generated by the evacuated ingestible device can also be used to determine whether the extension shaft 312' is in close proximity to the ingestible device for retrieval. Various methods of proximity sensing can be implemented, including but not limited to metal/magnetic means, electrical, sound/vibration (e.g. an audio signal), light (e.g. a color, visible light or infrared signal), electromagnetic radiation (e.g. an RF signal). As such the beacon signal, depending on the implementation, can be any one of these categories of signals. Proximity can also be determined, for example, based on the strength of the detected beacon signal which can be correlated to a distance with respect to the extension shaft 312'.

In some embodiments, at 806, the first signal that is sent to the ingestible device by the transceiver 334 can be used to optionally trigger the ingestible device to perform one or more functions such as (a) data transfer, (b) power mode selection and/or (c) sensing mode section. For the data transfer function, the controller 338 configures and sends the first signal, via the transceiver 334, to instruct the ingestible capsule to transmit data files to the recovery tool 300 or another suitable device. For the power mode section function, the controller 338 configures and sends the first signal, via the transceiver 334, to instruct the ingestible capsule to select a lower power mode to maintain power during shipment. For the sensing mode selection function, the controller 338 configures and sends the first signal, via the transceiver 334, to instruct the ingestible device to use only temperature sensors to monitor temperature during storage and/or shipping.

In some embodiments, the recovery tool 300 can also be configured to execute one or more functions once the ingestible device has been recovered such as entering a certain power mode and/or monitoring mode. For example, the controller 338 may be configured to operate the recovery tool 300 in low power mode upon retrieval of the ingestible device. Alternatively, the controller 338 may be configured to operate at least one of the sensors 336 for monitoring a condition of the ingestible device. As another example, the recovery tool 300 can be controlled by the controller 338 to enter a low power mode for transport and a temperature monitoring mode for monitoring the temperature of the ingestible device during transport.

Figure 4:
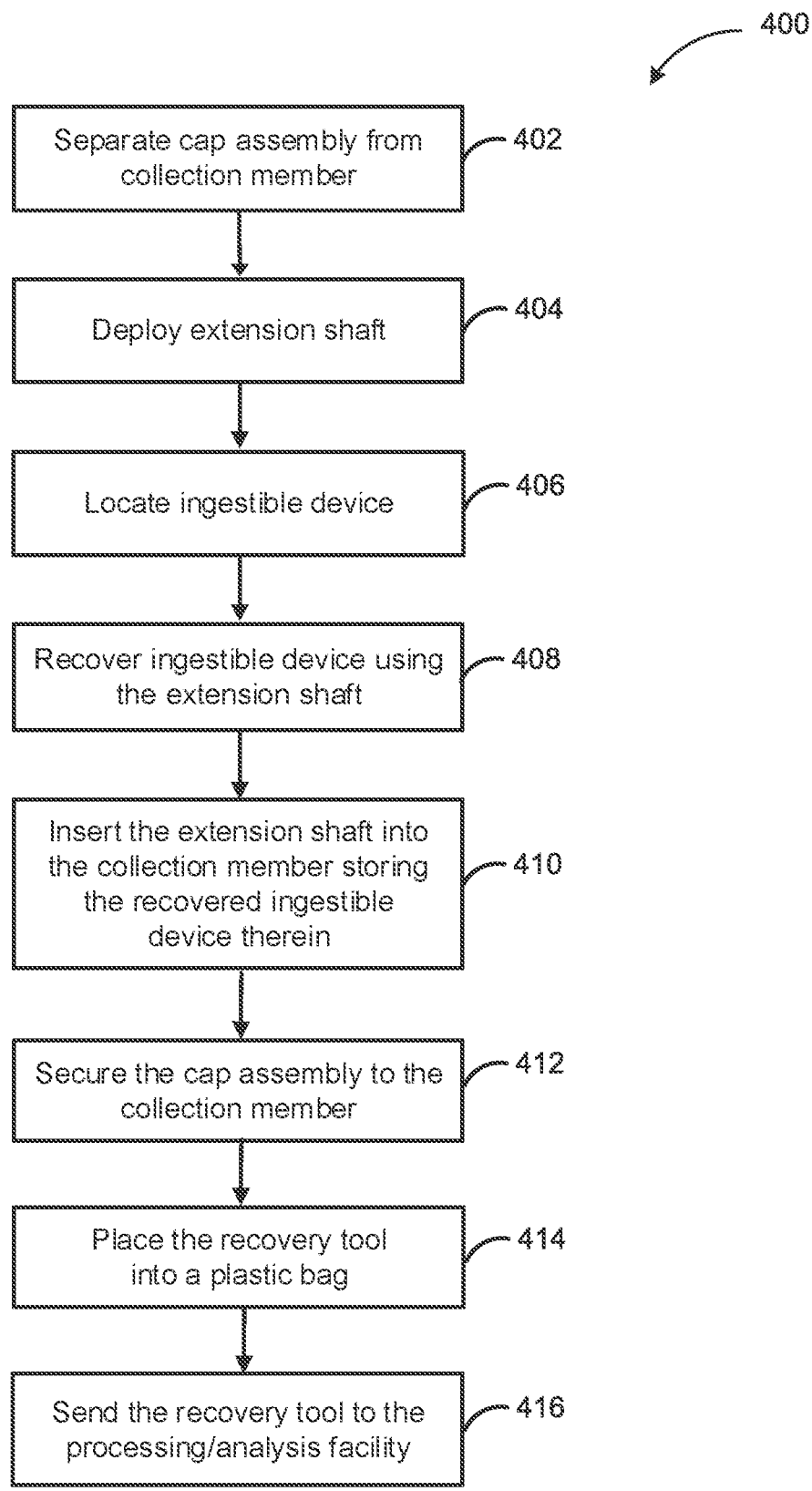
FIG. 4 is a flowchart of an example embodiment of a recovery method that can be used to recover an ingestible device using the recovery tools described herein.

Referring now to FIG. 4, shown therein is a flowchart showing an example embodiment of a recovery method 400 that can be used with the recovery tool 100 or 300 for recovering an evacuated ingestible device. FIGS. 5A-5M are the accompanying illustrations for the recovery method 400 where the illustrations depict the physical actions that can be performed when an ingestible device is being recovered using one the recovery tools described herein. For ease of illustration, the method 400 will be described with respect to using recovery tool 300.

Figure 5A:
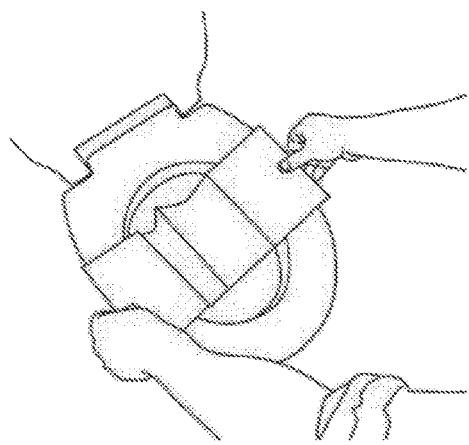
FIGS. 5A-5M are diagrams depicting the physical actions that can be performed when an ingestible device is being recovered using at least one the recovery tools described herein.

The method 400 begins upon expecting that the ingestible device will soon be evacuated and therefore a person wishing to retrieve the ingestible device, who may be the user who has ingested the ingestible device, hereafter referred to as the retrieval person, prepares a collection tray and mounts it on a toilet as is shown in FIG. 5A. The user who ingested the ingestible device then has a bowel movement and defecates on the collection tray. In some cases, the retrieval person may use a device, such as a smart phone, or their visual or auditory senses, depending on the form of the beacon signal, to detect that a beacon signal has been generated and emitted when the ingestible device detects that it has evacuated the user's body and is now included in the excreted fecal matter. Alternatively, the retrieval person can visually inspect the evacuated fecal matter to determine if the ingestible device has evacuated the user's body.

Figure 5B:
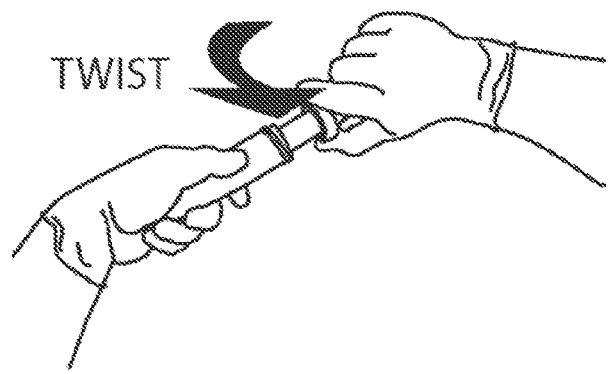

At act 402, once it has been determined that the ingestible device has evacuated the user's body, the retrieval person separates the cap assembly 304 from the collection member 302, as shown in FIG. 5B. The collection member 302 and the cap assembly 304 may initially be releasably secured together by being screwed together to be a compact unit. As such the retrieval person has to unscrew the cap assembly 304 from the collection member 302. For other embodiments in which other securing mechanisms have been used to releasably secure the cap assembly 304 to the collection member 302, the retrieval person will have to perform a corresponding action to remove the cap assembly 304 from the collection member 302.

Figure 5C:
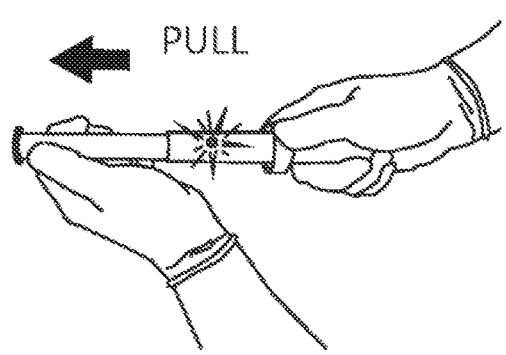

At act 404, the extension shaft 312' may be extended into the extended position by the retrieval person who pulls the lip 316 away from the shaft 312 while holding onto the handle 310 of the cap assembly 304 as shown in FIG. 5C. The shaft 312' exits the shaft 312 by moving outwardly away from the closure portion 308 until the boss 320 protrudes through the opening 318 of the shaft 312 to secure the extension shaft 312' in place as shown in FIG. 5C. In some embodiments, the retrieval person may prefer not to extend the extension shaft 312' and may choose to recover the ingestible device with the extension shaft 312' in its retracted position (or this may be done because there may be some embodiments in which there is no extension shaft 312'). Act 404 may be slightly different if the locking mechanism provided by the boss 320 is implemented differently as explained previously.

Figure 5D:
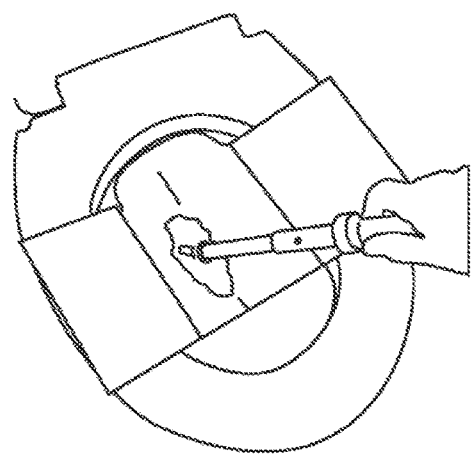

At act 406, the ingestible device is located among the excreted bowel movement. As described earlier, the sensors 336 can include a proximity sensor to determine the proximity of the evacuated ingestible device. For example, the proximity sensor can determine the strength of a beacon signal that is transmitted by the evacuated ingestible device. The signal strength may be proportionate to a separation distance separating the evacuated ingestible device and the cap assembly 304. In some cases, the ingestible device may generate a visual signal (i.e. flashing lights) or an audio signal (beeping sound) so as to allow the retrieval person to visually or aurally identify the location of the evacuated ingestible device. As shown in FIG. 5D the use of extension shaft 312' may be advantageous as the retrieval person may engage the extension shaft 312' to separate the excreted fecal matter resting in the toilet-mounted collection tray if the evacuated ingestible device may be located under or within a layer of fecal matter.

At act 408, the evacuated ingestible device is located and recovered using the distal end of the shaft 312 (if the extension shaft 312' is in the retracted position) or the distal end of the extension shaft 312' if the extension shaft 312' is in the extended position. As described previously, a magnet may be embedded at the distal end of the shaft 312/extension shaft 312' to apply a magnetic force to the evacuated ingestible device so that the retrieval person can pick up the evacuated ingestible device without having to directly contact the excreted fecal matter.

It should be noted that in alternative embodiments, the recovery tool 300 can have other implementations for the means that is used to retrieve the ingestible device, hereafter referred to as a retriever. For example, the retriever can include the magnet 124. Alternatively, the retriever can include a mechanical means such as extending mechanical forceps, graspers or a pliable loop having a diameter slightly smaller than that of the ingestible device to grab the ingestible device during recovery, adhesive means such as tape for attaching to the ingestible device during recovery, or a suction tip or a vacuum for sucking up the ingestible device during recovery. Alternatively, the retriever may include at least two of the retrieval means previously mentioned.

In an alternative embodiment, after the ingestible device has been retrieved using the recovery tool 300, a rotation function can be optionally performed with the recovery tool 300 to rotate the shaft 312 (and/or the extended shaft 312') to allow for cleaning of the ingestible device (e.g., when the toilet flushes, etc.) or positioning of ingestible device in the collection chamber 302c. In this case, the recovery tool has a rotational actuation member (not shown) that can be actuated by the user to perform the rotating function. The rotational actuation member can be implemented using a gear assembly in the upper portion of the cap assembly 304.

Figure 5E:
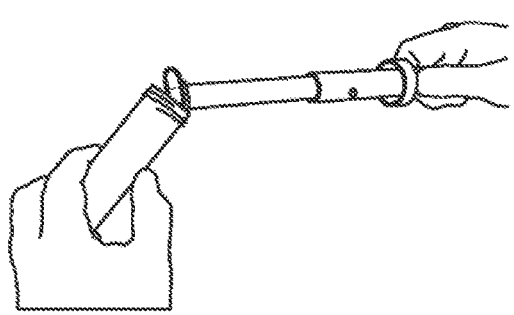
Figure 5F:
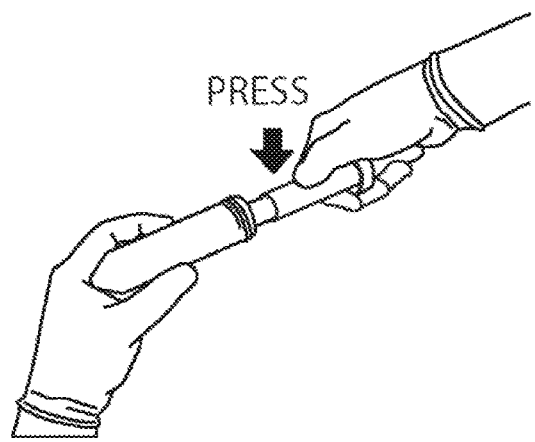
Figure 5G:
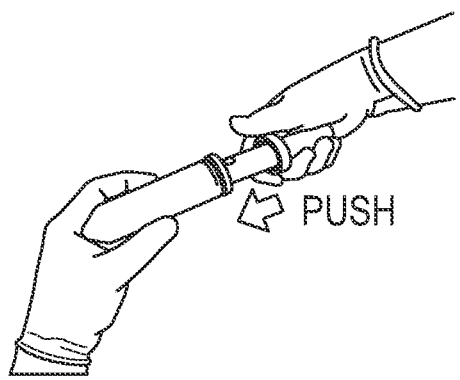

At act 410, the recovered ingestible device, being now attached to the distal end of the shaft portion 312, is placed into the collection chamber 302c, as shown in FIG. 5E, when the retrieval person inserts the extension shaft 312' while in extended position (or in a retracted position depending on how the retrieval person has used the recovery tool 300 to pick up the evacuated ingestible device) into the collection chamber 302c. If the extension shaft 312' is in the extended position, then the retrieval person may have to depress the boss 320, as is shown in FIG. 5F, so that the extension shaft 312' slides into the shaft 312 as the retrieval person is placing the extension shaft 312' into the collection chamber 302c and the distal end of the extension shaft 312' is pushed against an inner wall of the collection chamber 302c, as is shown in FIG. 5G. Alternatively, in other embodiments, the extension shaft may be spring loaded in such that when the button 320 is depressed, the extension shaft 312' may automatically retract. The retraction may be dampened to minimize excess force being exerted onto the recovered ingestible device.

In some alternative embodiments of the recovery tool 300, after act 410, power may be provided to the ingestible device from the power source 330. For example, wireless charging may be used.

Alternatively, or in addition to providing power to the ingestible device, in some alternative embodiments of the recovery tool 300, data may be downloaded from the ingestible device to the memory 332. In these embodiments, the transceiver 334 receives the data to be downloaded from the ingestible device when the ingestible device has been retrieved by the recovery tool 300 or when the ingestible device has been located by the recovery tool 300 (as explained previously through various signaling mechanisms) and the ingestible device is in close enough proximity so that the transceiver 334 can accurately receive the data from the ingestible device.

Figure 5H:
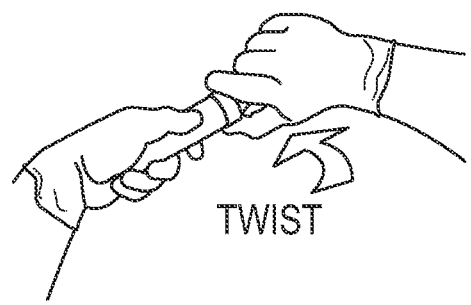

At act 412, the collection chamber 302c is sealed by securing the closure portion 308 of the cap assembly 304 to the collection member 302. For a screw-on cap embodiment, the cap assembly 304 may be secured onto the collection member 302, as is shown in FIG. 5H, by mounting the closure portion 308 onto the threaded portion 306 of the collection member 302 and performing a turning motion in the same manner as screwing on a bottle cap, for example.

Figure 5I:
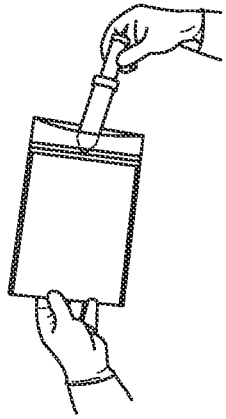

If the retrieval of the evacuated ingestible device is done at a location that is remote relative to the processing/analysis facility where the evacuated ingestible device is analyzed, then the retrieval person may insert the recovery tool 300 containing the evacuated ingestible device into a plastic bag at act 414, as is shown in FIG. 5I for transport to the processing/analysis facility.

Figure 5J:
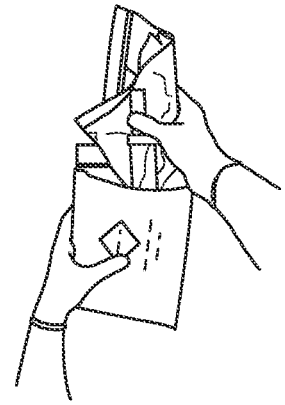
Figure 5K:
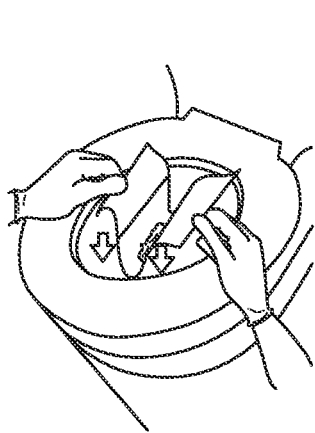
Figure 5L:
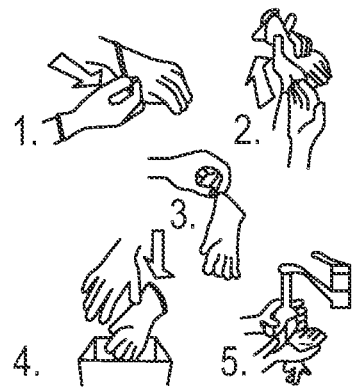
Figure 5M:
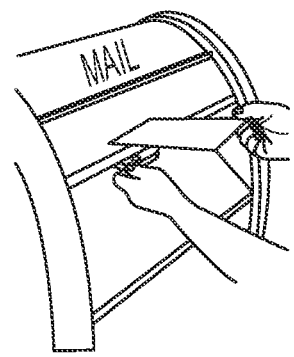

In instances where the recovery tool 300 containing the evacuated ingestible device must be shipped to the processing/analysis facility, the retrieval person may insert the plastic bag into a shipping package at act 416, as is shown in FIG. 5J. The materials used to recover the evacuated ingestible device can then be disposed of and the retrieval person may wash their hands and clean up, as is shown in FIGS. 5K and 5L. The shipping package can then be sent in the mail, as is shown in FIG. 5M, or by courier or some other transport method to the processing/analysis facility.

The shipping package along with the ingestible device recovery tool 300 may be required to be compliant with rules and regulations respecting the shipment of biological samples. For example, in the present embodiment, the shipping package may be selected and the recovery tool 100 and 300 may be made using materials that are compliant with UN3373 regulations related to medical packaging and shipment of category B materials (human or animal specimens).

Figure 6A:
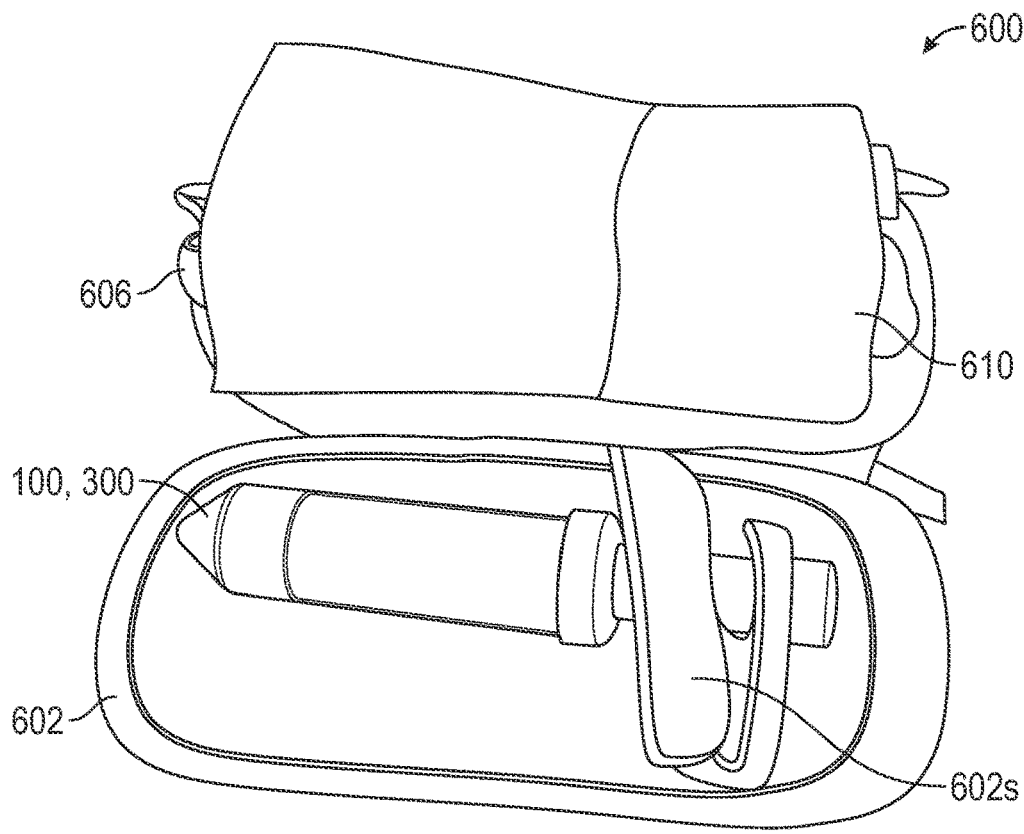
FIGS. 6A-6B are diagrams showing an example embodiment of a kit comprising the recovery tool and associated items for recovering an ingestible device.
Figure 6B:
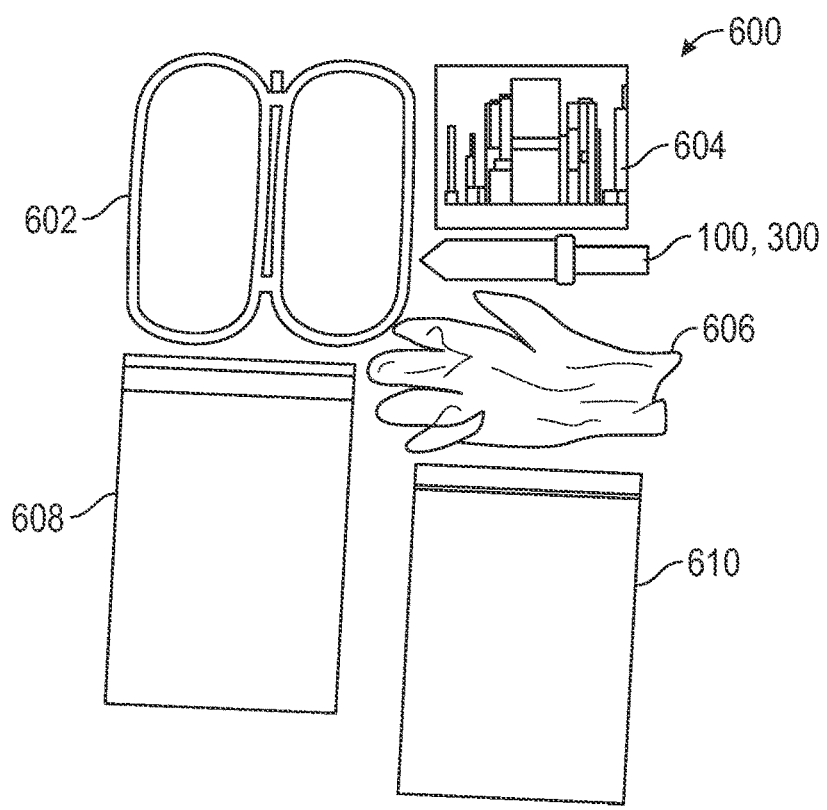

Referring now to FIGS. 6A-6B, shown therein are diagrams of an example embodiment of an ingestible device recovery kit 600 comprising the recovery tool 100 or 300 and associated items for recovering an ingestible device. For example, the kit 600 comprises a package or carrying case 602, instructions 604 for using the recovery tool 100 or 300, gloves 606 for handling the recovery tool 100 or 300 during the evacuated device retrieval process, a plastic bag or package 608 for holding the recovery tool 100 or 300 when it is containing the retrieved ingestible device and a shipping package 610. The instructions 604 may be printed on paper. The carrying case 602 can be made from suitable natural or synthetic materials. The contents of the ingestible device recovery kit 600 may be collectively referred to as an ingestible device recovery system.

Although not shown in FIGS. 6A-6B, the kit 600 may further comprises a collection tray that can be mounted on the toilet before for collecting fecal matter than contains the evacuated ingestible device. In an alternative embodiment, the kit 600 may also include sturdy packaging materials such as one or two thin layers of bubble-wrap or one or two thin layers of foam that can be included in the "shipping package" and between which the recovery tool 300 may be inserted for shipping. Accordingly, the sturdy packaging materials can be used to protect the recovery tool and the retrieved ingestible device during shipping. Alternatively, the shipping package 610 may be made of a sturdy material.

The kit 600 comprises all of the necessary components to ensure the shipping of a human, clinical sample is compliant with federal and local requirements, including the use of a watertight primary receptacle, a watertight secondary receptacle, and absorbent material. In some embodiments the shipping package 610 comprises appropriate markings. The recovery tool 300 acts as the watertight primary receptacle and the plastic bag/package 608 acts as the watertight secondary receptacle in accordance with UN3373 regulations. Accordingly, the recovery tool 100/300 is made according to UN 3373 regulations. In embodiments, which include the sturdy packaging materials, they can be also be made of an absorbent material or include an absorbent layer to absorb fluids in case there is a leak. Alternatively, the shipping package 610 may be include an absorbent material that is absorbs fluids in case there is a leak.

Figure 7A:
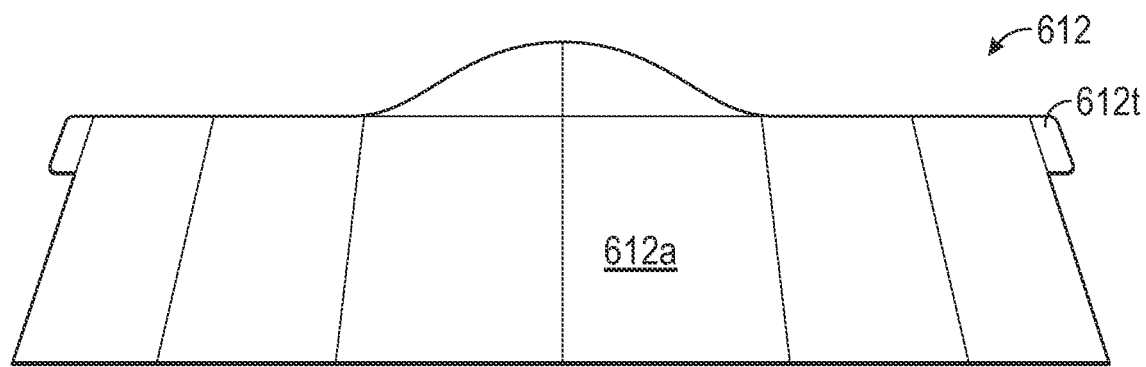
FIGS. 7A-7C are diagrams of an example embodiment of a collection tray that can be used to collect fecal matter than contains an ingestible device after it has evacuated the body of a user, wherein said ingestible device can be subsequently retrieved from the collection tray using at least one of the recovery tools, kits and methods described herein.
Figure 7B:
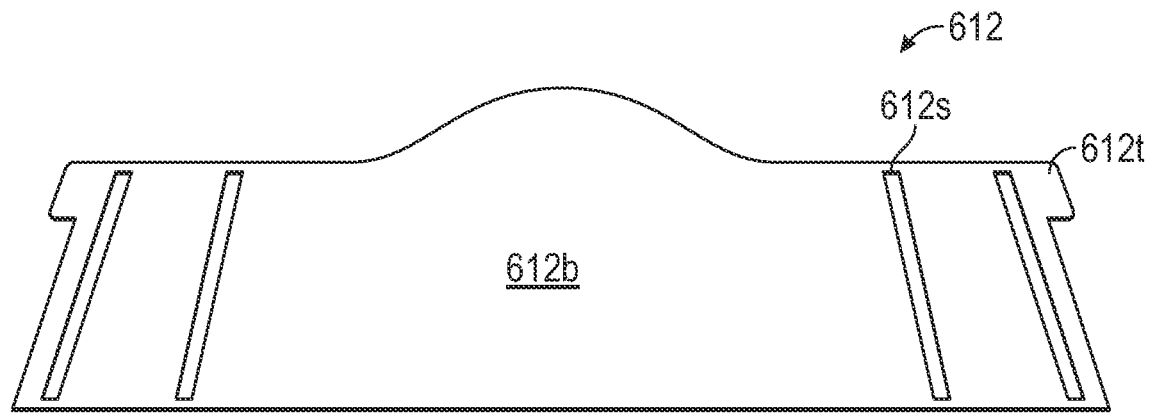
Figure 7C:
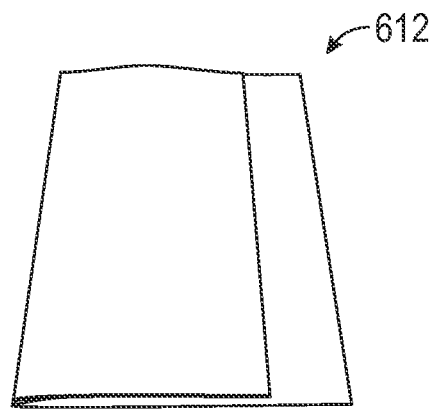

Referring now to FIGS. 7A-7C, shown therein are diagrams of an example embodiment of a collection tray 612 that can be used to collect fecal matter than contains an ingestible device after it has evacuated the user's body. FIGS. 7A-7B show views of the upper and lower surfaces of the collection tray 612 when unfolded. FIG. 7C shows a view of the collection tray 612 in a folded configuration that is used when the collection tray 612 is in the kit 600. The collection tray 612 is a paper sheet that is thick enough to provide the strength to collect fecal matter but is also thin enough to allow it to be easily flushed in the toilet after the ingestible device has been retrieved. In alternative embodiments, the collection tray 612 can be made from a rigid or semi-rigid material that can be collapsed so that the collection tray 612 can fit within the kit 600. In some embodiments, the instructions may be printed on a surface of the collection tray 612.

In some embodiments, the kit 600 may include an additional collection item (not shown) to provide support for the collection tray 612. The additional collection item may be in the form of a mesh, a net or a screen that allows liquid and solid waste to pass therethrough but not the ingestible device. The additional collection item may be placed on the central portion of the collection tray 612 after the collection tray has been attached to a toilet or other fecal collector.

In some embodiments, the collection tray 610 may not be included in the kit 600 such as in cases where the recovery kit is used to recover evacuated ingestible devices from animals.

The collection tray 610 has a top surface 612a and a bottom surface 612b. The bottom surface 612b comprises several adhesive strips 612s (only one of which is labelled for simplicity) that are covered with removable backings (made of paper or coated plastic, for example). The backings are removed to expose the adhesion portion of the adhesive strips 612s and the bottom surface 612b of the collection tray 612 is mounted on a toilet seat such that the adhesive strips stick to the top of the toilet seat and a mid-portion of the collection tray 612 hangs below the upper surface of the toilet seat, as is shown in FIG. 5A, such that there is enough room for the user of the ingestible device to defecate onto the collection tray 612 without the evacuated fecal matter contacting the user as it is deposited onto mid-portion of the collection tray 612. The collection tray 612 also comprises removal tabs 612t (only one of which is labelled for simplicity) that the retrieval person may pull on when removing the collection tray 612 from the toilet seat. The collection tray 612 may then be flushed down the toilet. Accordingly, the collection tray 612 is generally foldable and may be flushable.

In this example embodiment, there are four adhesive strips 612s to provide a stronger and more stable attachment between the collection tray 612 and the toilet. This is done by using the two inner adhesive strips to attach portions of the collection tray 612 to the toilet seat and using the two outer adhesive strips to attach portions of the collection tray to the toilet bowl. Accordingly, the backings of the two inner adhesive strips are removed first to expose the inner adhesive surfaces which are then adhered to the toilet seat by pressing firmly on the portions of the top surface 612a of the collection tray 612 that are directly over the inner adhesive strips to attach these two adhesive strips on top of corresponding sides of the toilet seat. The backings of the two outer inner adhesive strips are then removed to expose the inner adhesive surfaces which are then adhered to the toilet bowl by pressing firmly on the portions of the top surface 612a of the collection tray 612 that are directly over the outer adhesive strips to attach these two adhesive strips to corresponding sides of the toilet bowl.

Various components of the kit 600 (e.g.: the recovery tool, the shipping package, and the collection tray) can be designed and packaged in a discrete way so that the kit 600 is inconspicuous if seen by others who are not using the kit 600. For example, the kit 600 can be designed and packaged to resemble a toiletry bag or a neoprene laptop case. The packaging of the kit 600 and some of the internal components may also be varied for male and female users so that it is appealing and publically discrete. For example, the recovery tool can be designed to appear similar to a tooth brush or other toiletry that may go unnoticed in public settings.

At least one of the example embodiments of the recovery tool and the associated recovery methods and kits described herein may make it easier to retrieve an evacuated ingestible device and send it to a processing/analysis facility since. For example, there are a reduced number of steps which also makes it less likely for the retrieval person to fail recovering the ingestible device. The recovery tool also makes it possible for the retrieval person to recover the evacuated ingestible device without having direct contact with fecal matter. The ingestible device recovery kit is also portable, discrete, and usable in public facilities.

In another alternative embodiment, after the retriever has retrieved the evacuated ingestible device and prior to inserting the extension shaft into the collection chamber, for embodiments in which the recover tool comprises a rotational actuator member, the retrieval person may rotate or gently spin the extension shaft to remove some of the fecal matter on the outer housing of the retrieved ingestible device. The retriever may be inserted into the toilet bowl water and the extension shaft rotated to aid in this cleansing act. Alternatively, or in addition thereto, when the retriever is in the toilet bowl water, the toilet bowl may be flushed to aid in cleansing the outer surface of the recovered ingestible device. Alternatively a separate container may be filled with a cleansing fluid (e.g. water) and poured onto the recovered ingestible device to wash it. This acts of inserting the retriever in the toilet bowl water, possibly flushing the toilet and possibly using a separate container to pour cleansing fluid onto the recovered ingestible device may be performed for embodiments of the recovery tool which do not include a rotational actuation member.

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

The invention claimed is:

1. A recovery tool, comprising:
a collection member having an open end, a closed end and a collection chamber between the open end and the closed end, the collection chamber configured to receive an ingestible device; and
a cap assembly releasably attachable to the open end of the collection member to seal the collection chamber, the cap assembly comprising:
a closure portion;
a handle extending from the closure portion in a first direction;
a shaft extending from the closure portion in a second direction that is opposite the first direction;
a retriever disposed at a distal end portion of the shaft and adapted to retrieve the ingestible device;
a controller to control one or more electronic aspects of the recovery tool; and
at least one sensor coupled to the controller and operable to detect a parameter of the environment of the collection chamber after storage of the retrieved ingestible device.

2. The recovery tool of claim 1, further comprising an extension shaft moveably coupled to the shaft and having a distal end portion, the extension shaft being moveable between a retracted position in which the extension shaft is disposed within the shaft and an extended position in which the distal end portion of the extension shaft is extended away from the shaft in a telescopic manner.

3. The recovery tool of claim 2, wherein the extension shaft is slidably coupled to the shaft so that the extension shaft is moveable in a telescopic fashion.

4. The recovery tool of claim 2, wherein the extension shaft comprises at least two sections that are pivotally coupled to one another so that the extension shaft is moveable in a pivotable fashion.

5. The recovery tool of claim 1, wherein the retriever comprises a magnet disposed in the distal end portion of the extension shaft and adapted to retrieve the ingestible device by applying a magnetic attraction force.

6. The recovery tool of claim 1, wherein the retriever comprises at least one member selected from the group consisting of mechanical forceps, graspers, a pliable loop, adhesive means, a suction tip and a vacuum.

7. The recovery tool of claim 1, further comprising a locking mechanism adapted to maintain an extension shaft in a retracted position, wherein the locking mechanism is actuable so that the extension shaft is moveable to an extended position.

8. The recovery tool of claim 1, wherein, when the extension shaft is in the extended position, the extension shaft is moveable to the retracted position by pushing a distal end of the cap assembly against an inner portion of the collection chamber.

9. The recovery tool of claim 1, wherein the collection member and the cap assembly define a seal when releasably secured to one another to prevent any fluid from escaping from or entering into the collection chamber.

10. A recovery kit, comprising:
the recovery tool according to claim 1; and
a carrying case dimensioned to receive the recovery tool.

11. A recovery tool, comprising:
a collection member having an open end, a closed end and a collection chamber between the open end and the closed end for receiving an ingestible device after recovery; and
a cap assembly releasably attachable to the open end of the collection member to seal the collection chamber, the cap assembly comprising:
a sensor configured to receive a beacon signal from the ingestible device and detect a proximity of the ingestible device;
a transceiver configured to transmit a signal to the ingestible device; and
a shaft extending from the closure portion to retrieve the ingestible device.

12. The recovery tool of claim 11, further comprising an extension shaft moveably coupled to the shaft and having a distal end portion, wherein the extension shaft is moveable between a retracted position in which the extension shaft is disposed within the shaft and an extended position in which the distal end portion of the extension shaft is extended away from the shaft in a telescopic or pivotal manner.

13. The recovery tool of claim 11, wherein an extension shaft is slidably coupled to the shaft allowing the extension shaft to be moveable in a telescopic fashion.

14. The recovery tool of claim 11, further comprising: a retriever attached at an end of the shaft, the retriever comprising a magnet disposed in a distal end portion of an extension shaft and adapted to retrieve the ingestible device by applying a magnetic attraction force.

15. The recovery tool of claim 11, further comprising a locking mechanism that maintains an extension shaft in a retracted position and is actuable to allow movement of the extension shaft to an extended position.

16. The recovery tool of claim 11, further comprising a controller to control one or more electronic aspects of the recovery tool, wherein the sensor is coupled to the controller and operable to detect a parameter of the environment of the collection chamber after storage of the ingestible device.

* * * * *